United States Patent [19]

Shinzaki et al.

[11] Patent Number: 5,166,049
[45] Date of Patent: Nov. 24, 1992

[54] MEASUREMENT OF DIAPHORASE ACTIVITY AND REAGENT THEREFOR

[75] Inventors: Akihiro Shinzaki; Mihoko Era; Naoko Kenmotsu; Tadao Suzuki, all of Kyoto, Japan

[73] Assignee: Unitika Ltd., Hyogo, Japan

[21] Appl. No.: 610,679

[22] Filed: Nov. 8, 1990

[30] Foreign Application Priority Data

Nov. 8, 1989 [JP] Japan ................................. 1-290453
Dec. 7, 1989 [JP] Japan ................................. 1-320111

[51] Int. Cl.$^5$ .......................... C12Q 1/00; C12N 9/00
[52] U.S. Cl. ..................................... 435/4.0; 435/25; 435/26; 435/189; 435/291; 435/810; 435/19; 422/61; 422/68.1
[58] Field of Search .................... 435/4.0, 25, 26, 189, 435/291, 810, 19; 422/61, 68.1

[56] References Cited

U.S. PATENT DOCUMENTS 4,622,296 11/1986 Yamanishi et al. ................. 435/184
4,889,797 12/1989 Amano et al. ...................... 435/805

*Primary Examiner*—Johnnie R. Brown
*Assistant Examiner*—Pamela S. Webber
*Attorney, Agent, or Firm*—Sughrue, Mion, Zinn, Macpeak & Seas

[57] ABSTRACT

A method for measuring diaphorase activity comprising mixing a sample comprising diaphorase with nitro blue tetrazolium, EDTA or a salt thereof, at least one of nicotinamide adenine dinucleotide and nicotinamide adenine dinucleotide phosphate, and a surface active agent, to form an assay solution; and measuring an increase in absorbance, due to the formation of diformazan, in the assay solution and reagents used in a method for measuring diaphorase activity comprising a first solution, a second solution, EDTA, and a surface active agent, wherein the first solution comprises at least one of nicotinamide adenine dinucleotide or nicotinamide adenine dinucleotide phosphate and the second solution comprises nitro blue tetrazolium.

20 Claims, 2 Drawing Sheets

MEASUREMENT OF DIAPHORASE ACTIVITY AND REAGENT THEREFOR

FIELD OF THE INVENTION

This invention relates to methods for measuring diaphorase activity using nitro blue tetrazolium (hereinafter abbreviated as NBT) as a substrate and to reagents for measurement of diaphorase activity. The present invention enables one to accurately and sensitively detect diaphorase.

BACKGROUND OF THE INVENTION

Diaphorase is an enzyme catalyzing the reduction of a pigment with nicotinamide adenine dinucleotide (hereinafter abbreviated as NADH) or nicotinamide adenine dinucleotide phosphate (hereinafter abbreviated as NADPH) (the abbreviation NAD(P)H will hereinafter be used to denote either one of NADH and NADPH).

Measurements of diaphorase activity have generally been made by colorimetrically analysis of changes in absorbance which accompany reduction of pigments. Pigments reducible in the presence of diaphorase include, e.g., dichlorophenolindophenol (hereinafter abbreviated as DCIP) and NBT.

In using DCIP as a reducible pigment (substrate), DCIP has an absorption at a wavelength of 600 nm and is reduced with NAD(P)H to reduced-DCIP having no absorption at 600 nm, and the decrease in absorbance at 600 nm is thus used to assay diaphorase activity (*Biochem. J.*, Vol. 191, pp. 457–465 (1980)). In this method, it is necessary to start measurement with a pigment solution having a high absorbance. Therefore, the absorbance at 600 nm at the start of measurement is not constant, and varies for each measurment. Further, even with no enzyme present in the solution, DCIP is reduced with NAD(P)H through non-enzymatic reaction which also causes reduction in absorbance at 600 nm.

Alternatively, measurement of diaphorase activity using NBT can be effected by measuring the increase in absorbance at 550 nm due to the formation of diformazan by the reduction of NBT. Accordingly, any pigment solution should have zero absorbance at 550 nm at the start of measurement. A method using NBT as a substrate therefore achieves more accurate diaphorase assay results than one using DCIP as a substrate. For this reason, when diaphorase is used when sensitivity and accuracy are of importance, for example, in an enzyme immunoassay, NBT is used as a substrate more widely than DCIP (see, e.g., JP-A-60-214900 and JP-A-60-58097 (the term "JP-A" as used herein means an unexamined published Japanese patent application)).

In spite of the above-described advantages, NBT is also known to suffer from problems, such as being non-enzymatically converted to diformazan in the presence of NAD(P)H, causing the absorbance at 550 nm to gradually increase. Therefore, when measuring diaphorase activity using NBT, a solution containing diaphorase and a blank solution containing no diaphorase are assayed to determine the increase of absorbance in each solution, and the increase in absorbance of the blank solution is substracted from that of the NBT solution. That is, the measured value is the sum of the increase in absorbance arising from (A) the enzyme reaction of diaphorase and (B) the non-enzymatic action of the blank so that subtraction of the blank value from the measured value gives more accurate and precise diaphorase activity. However, such a method of measurement, when a small amount of diaphorase is assayed, suffers from the additional problem that the ratio of the blank value to the true value attributed to enzyme reaction becomes high, so that the blank value can be many fold higher than that of the enzyme activity value, thus making it difficult to provide an accurate measurement of diaphorase activity even when a blank solution is used.

SUMMARY OF THE INVENTION

An object of this invention is to provide methods for measuring diaphorase activity, with increased accuracy, specificity and precision such that accurate and precise measurements can be made of even very small amounts or concentrations of diaphorase by depressing blank values and increasing absorbance values as indicative of diaphorase activity.

Another object of the present invention is to provide reagents which can be used in the herein-described methods.

A further object of the present invention is to provide methods for measuring diaphorase activity, with which diaphorase activity values are increased to obtain accurate diaphorase activity values with increased sensitivity and wherein the adsorption of diformazan onto a plastic solid phase is reduced or substantially eliminated.

A further object of the present invention is to provide methods for measuring diaphorase activity, using NBT in which a solution under assay contains EDTA or a salt thereof and to reagents therefor.

A still further object of the present invention is to provide methods and reagents for measuring diaphorase activity using NBT in assay solutions which contain EDTA and cationic surface active agents comprising a straight chain aliphatic saturated hydrocarbon containing from 14 to 28 carbon atoms having a terminal trimethylammonium group, (hereinafter TACD).

A further object of the present invention is to provide methods and reagents wherein blank values are appreciably depressed so that diaphorase activity can be measured with increased accuracy sensitivity and precision.

A further object of the present invention is to provide methods wherein a plastic solid phase can be employed in such measurement systems such that adsorption of diformazan onto solid phases is substantially eliminated or significantly reduced so that measurements can be made which have superior accuracy, sensitivity and precision over methods lacking EDTA and/or TACD.

The above objects of the present invention have been met by a method for measuring diaphorase activity comprising mixing a sample comprising diaphorase with nitro blue tetrazolium, EDTA or a salt thereof, at least one of nicotinamide adenine dinucleotide and nicotinamide adenine dinucleotide phosphate, and a surface active agent, to form an assay solution; and measuring an increase in absorbance, due to the formation of diformazan, in the assay solution.

The above objects of the present invention have also been met by the above methods, wherein the surface active agent is a cationic surface active agent comprising a straight chain aliphatic saturated hydrocarbon, wherein the hydrocarbon comprises from 14 to 28 carbon atoms and has a terminal trimethylammonium group.

The above objects of the present invention have also been met by reagents for measuring diaphorase activity comprising a first solution, a second solution, EDTA, and a surface active agent, wherein the first solution comprises at least one of nicotinamide adenine dinucleotide or nicotinamide adenine dinucleotide phosphate and the second solution comprises nitro blue tetrazolium.

BRIEF DESCRIPTION OF THE DRAWINGS

In FIG. 2, black dot marks indicate absorbance relative to diaphorase activity including blank values when assay solutions contain EDTA, and white dot marks indicate absorbance relative to diaphorase activity including blank values when an assay solutions contain no EDTA.

In FIG. 3, black dot marks and black triangle marks indicate diaphorase activity when assay solutions contain cetyltrimethylammonium bromide (hereinafter abbreviated as CTAB) (as a TACD surface active agent) and EDTA and when assay solutions contain stearyltrimethylammonium chloride (hereinafter abbreviated as STAC) (as a TACD surface active agent) and EDTA, respectively, and white dot marks indicate diaphorase activity when assay solutions contain Triton X-100 as a surface active agent.

In FIG. 4, black dot marks indicate absorbance relative to diaphorase activity including blank values when assay solutions contain CTAB (as a TCAD surface active agent) and EDTA, and white dot marks indicate absorbance relative to diaphorase activity including blank values when assay solution contain Triton X-100 as a surface active agent.

DETAILED DESCRIPTION OF THE INVENTION

Figure 1:
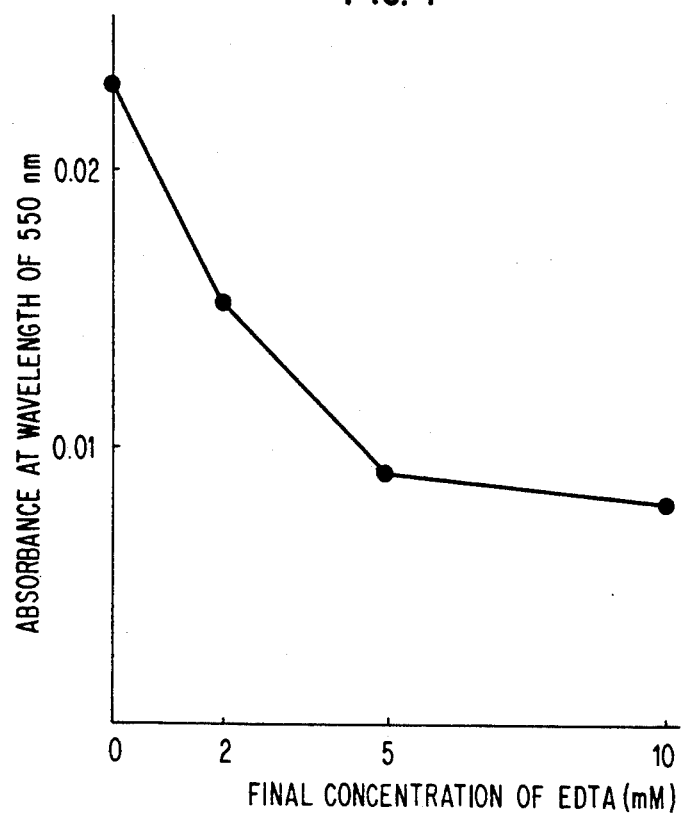
FIG. 1 is a graph showing the relationship between EDTA concentrations and blank values.

The inventors have conducted extensive investigations with the object of depressing blank values. As a result, it has now been found that blank values decrease when ethylenediaminetetraacetic acid or a salt thereof (hereinafter, "EDTA") is added to an assay solution.

The inventors also conducted extensive investigations with the object of increasing diaphorase activity and, at the same time, eliminating adsorption of diformazan onto plastic solid phases. As a result, methods and reagents have been found that substantially reduce blank values and increase diaphorase activity absorbance values, while also substantially reducing adsorption of diformazan onto plastic solid phases. Such methods and reagents provide the above-mentioned unexpectedly superior results by incorporating into the assay solutions EDTA and a cationic surface active agents comprising a straight chain aliphatic saturated hydrocarbon containing from 14 to 28 carbon atoms having a terminal trimethylammonium group, in place of Triton X-100 which has been conventionally used as a surface active agent.

In carrying out measurements of diaphorase activity, a sample containing diaphorase is mixed with NBT, EDTA, NAD(P)H, a surface active agent, a buffering solution, and other components to prepare a solution for measurement, and an increase of absorbance due to diformazan formation by reduction of NBT is determined.

EDTA which can be used in the present invention includes free acids and arbitrary salts thereof, e.g., potassium salts and sodium salts. A suitable EDTA final concentration in a solution for measurement ranges from about 1 to 50 mM, and preferably from about 3 to 10 mM.

Components in the solution other than EDTA are selected from those used in conventional methods for diaphorase measurement, as described below.

Buffering solutions which can be used in the present invention include those exhibiting a buffering action in the vicinity of neutrality, such as a phosphoric acid buffering solution and a triethanolamine buffering solution. The buffering solution preferably has a pH of from about 5 to 10, and more preferably from about 6 to 8. A suitable concentration of buffer in buffering solutions of assay solutions of the present invention ranges from about 10 to 500 mM, and preferably from about 50 to 100 mM.

A preferred NBT concentration in the solution under assay is from about 0.1 to 10 mM, and more preferably from about 0.2 to 1 mM.

NAD(P)H which can be used in the present invention may be either NADH or NADPH, with the former being preferred. A suitable NAD(P)H concentration in the solution ranges from about 0.1 to 5 mM, and preferably from about 0.5 to 2 mM.

Surface active agents which can be used in the present invention with the purpose of depressing blank values, though not particularly limited to these types, preferably include Triton series, with Triton X-100 being particularly preferred.

Surface active agents which can be used to increase diaphorase activity values and substantially eliminate or reduce adsorption of diformazan onto solid phases include TACD's in which the hydrocarbon comprises from 14 to 28 carbon atoms, preferably 14 to 18 carbon atoms. Specific examples of TACD's include myristyltrimethylammonium halides, cetyltrimethylammonium halides, stearyltrimethylammonium halides, arachidyltrimethylammonium halides, behenyltrimethylammonium halides, lignoceryltrimethylammonium halides, cerotyltrimethylammonium halides and montanyltrimethylammonium halides. Preferred of these are cetyltrimethylammonium chloride, CTAB, STAC and stearyltrimethylammonium bromide.

A suitable concentration of surface active agents in assay solutions of the present invention range from about 0.05 to 5 w/v %, and preferably from about 0.1 to 1 w/v %.

Diaphorase activity measurements according to the present invention should utilize assay solutions comprising diaphorase and the above-mentioned components at the start of measuring an increase in absorbance. The order of mixing these components is not particularly restricted.

Measurement of diaphorase activity according to the present invention can be effected as follows.

A diaphorase-containing sample is preferably prepared so as to contain from about 0.002 to 0.2 units of diaphorase per ml. To provide such a concentration, a sample is diluted, if necessary, with a buffering solution having a buffering action in the vicinity of neutrality so as to have a diaphorase concentration of not more than about 2 unit/ml, and the adjusted sample is used in an amount of about 100 μl or less.

To the thus concentration adjusted sample is added about 800 to 900 μl of a buffering solution containing EDTA, NAD(P)H, and a surface active agent in the respective concentrations, as recited above, to make 900 μl as a whole.

The resulting solution is then preliminarily incubated to a temperature of from about 20° to 40° C. A incubation time is the time for the solution to reach the above-recited temperature range, usually ranging from about 3 to 5 minutes.

To the preincubated solution is then added about 100 μl of an NBT solution having a concentration of from about 1 to 100 mM, and preferably from about 2 to 10 mM, followed by colorimetric determination.

Colorimetric determination can be conducted by a rate assay, in which an absorbance is measured over time and/or by an end-point assay in which absorbance is measured after an enzymatic reaction is continued for a given period of time and then stopped, and an enzyme activity is calculated from the change in absorbance. In either method of colorimetry, an absorbance at a wavelength between about 520 nm and 550 nm can be measured with a commercially available spectrophotometer. Stopping of the reaction in the end-point method is effected by using, for example, hydrochloric acid to reduce the pH of the solution, for example, to about 3 or less.

A blank can be run in the same manner as described above, except that diaphorase is excluded from the assay solutions.

Diaphorase which is suitably assayed by methods of the present invention is not particularly limited and includes, for example, diaphorase of bacterial origin and diaphorase of animal origin.

The terminology "one unit" of diaphorase as used herein means an enzyme amount which reduces 1 μmol of NBT per minute at a temperature of about 30° C. and at a pH of about 7.0 with Triton X-100 being used as a surface active agent.

Activity of diaphorase should be calculated according to the formula (1).

$$\text{Diaphorase activity (units)} = \frac{\Delta A \times V}{12.4 \times l} \quad (1)$$

wherein ΔA represents a change amount in absorbance per minute; V represents a total amount of reaction solution (ml); l represents a light pass length (cm) and 12.4 is the molar absorbance coefficient of NBT.

Reagents for activity measurement according to the present invention comprise the above-described components. Such reagents consist of two separately prepared solutions, one containing NBT and the other containing NAD(P)H, which solutions are mixed together to form assay solutions for carrying out measurement. For example, a reagent consists of Reagent A containing from about 2 to 100 mM of EDTA, from about 0.2 to 10 mM of NADH, and from about 10 to 500 mM of a buffering solution (pH=5 to 10) and Reagent B containing from about 0.2 to 20 mM of NBT, at least about 0.02 w/v % of a surface active agent, and from about 10 to 500 mM of a buffering solution (pH=about 5 to 10). Reagents A and B are mixed at a ratio of about 1:1 by volume for use.

The present invention is now illustrated in greater detail by way of Reference Examples, Examples, but it should be understood that the present invention is not limited thereto.

REFERENCE EXAMPLE 1

A solution having the following composition was prepared.

| | |
|---|---|
| 500 mM Triethanolamine-HCl (pH = 7.0) | 60 μl |
| 20 mM NADH | 60 μl |
| 1% Triton X-100 | 60 μl |
| H$_2$O | 300 μl |

To the resulting solution was added 60 μl of EDTA(-Na$_2$) having concentrations of 0, 20, 50 or 100 mM so as to have the final EDTA(Na$_2$) concentration of 0, 2, 5 or 10 mM, respectively. After incubation at 30° C. for 3 minutes, 60 μl of 5 mM NBT was added to the solutions, and enzymatic reactions were conducted at 30° C. The increase in absorbance at 550 nm was measured every minute to examine the effect of EDTA addition on blank control values. The results obtained are shown in Table 1 below and in FIG. 1.

TABLE 1

| | Final EDTA Concentration (mM) | | | |
|---|---|---|---|---|
| | 0 | 2 | 5 | 10 |
| Blank Value | 0.023 | 0.015 | 0.009 | 0.008 |

As can be seen from Table 1 and FIG. 1, blank values decreased as the EDTA concentration increased. The blank value at the final EDTA concentration of 5 mM was about two fifths that of the solution containing no EDTA.

EXAMPLE 1 AND COMPARATIVE EXAMPLE 1

A reagent for activity measurement containing EDTA in a final concentration of 5 mM (at which a blank depressive effect was exhibited as demonstrated in Reference Example 1) was prepared as follows.

Reagent A 50 mM Triethanolamine-HCl (pH=7.0)
4 mM NADH
10 mM EDTA

Reagent B 50 mM Triethanolamine-HCl (pH=7.0)
0.2% Triton X-100
1.0 mM NBT

For comparison, Reagent A' having the same composition as Reagent A, except for containing no EDTA, was prepared.

To 1 μl of samples containing 0, 1.0, 2.0, 3.0 or 4.0 mg of diaphorase (derived from *Bacillus thermophilus*, 120 unit/mg, molecular weight: 30,000) was added 300 μl of Reagent A or Reagent A', followed by incubation at 30° C. for 3 minutes. Then, 300 μl of Reagent B was added to the system. After incubation at 30° C. for 10 minutes, 150 μl of 1N HCl was added to stop the reaction, and the absorbance at 550 nm was measured. The results obtained are shown in Table 2 below and FIG. 2.

TABLE 2

| | | Diaphorase Content (ng) | | | | |
|---|---|---|---|---|---|---|
| Example No. | EDTA | (Blank value) 0 | 1.0 | 2.0 | 3.0 | 4.0 |
| Example 1 | added | 0.025 | 0.046 | 0.064 | 0.081 | 0.097 |
| Comparative Example 1 | not added | 0.045 | 0.071 | 0.090 | 0.106 | 0.124 |

Figure 2:
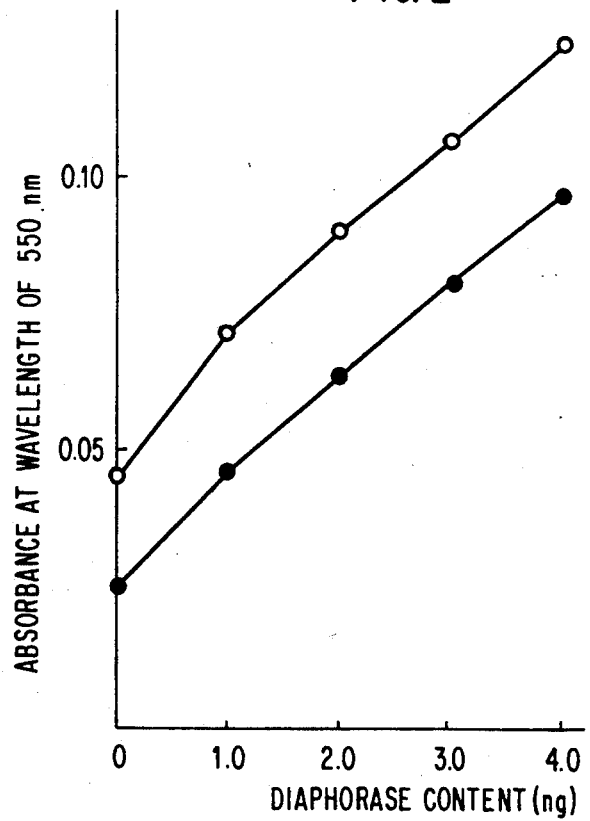
FIG. 2 is a graph showing the relationship between diaphorase amounts and absorbencies.

As is apparent from Table 2 and FIG. 2, the blank value (at a diaphorase content of 0 ng) of the EDTA-containing reagent system according to the present invention was reduced to five ninths of that of the comparative reagent system containing no EDTA. As a result, the enzyme activity, i.e., as shown by the absorbance value obtained by subtracting the blank value from the measured value, was substantially unchanged, and the proportion of the blank in the total absorbance was reduced, thus providing a more accurate detection of diaphorase.

EXAMPLES 2 TO 3 AND COMPARATIVE EXAMPLE 2

Three solutions having the following compositions were prepared.

| | |
|---|---|
| 500 mM Triethanolamine-HCl (pH = 7.0) | 60 μl |
| 20 mM NADH | 60 μl |
| Surface active agent selected from 1% Triton X-100 (Comparative Example 2), 5% CTAB containing 50 mM EDTA (Example 2), and 5% STAC containing 50 mM EDTA (Example 3) | 60 μl |
| $H_2O$ | 350 μl |
| Solution containing 0, 10, 20, 30 or 40 ng of diaphorase (originated in Bacillus tearothermophilus, 120 unit/mg, molecular weight: 30,000) | 10 μl |

Figure 3:
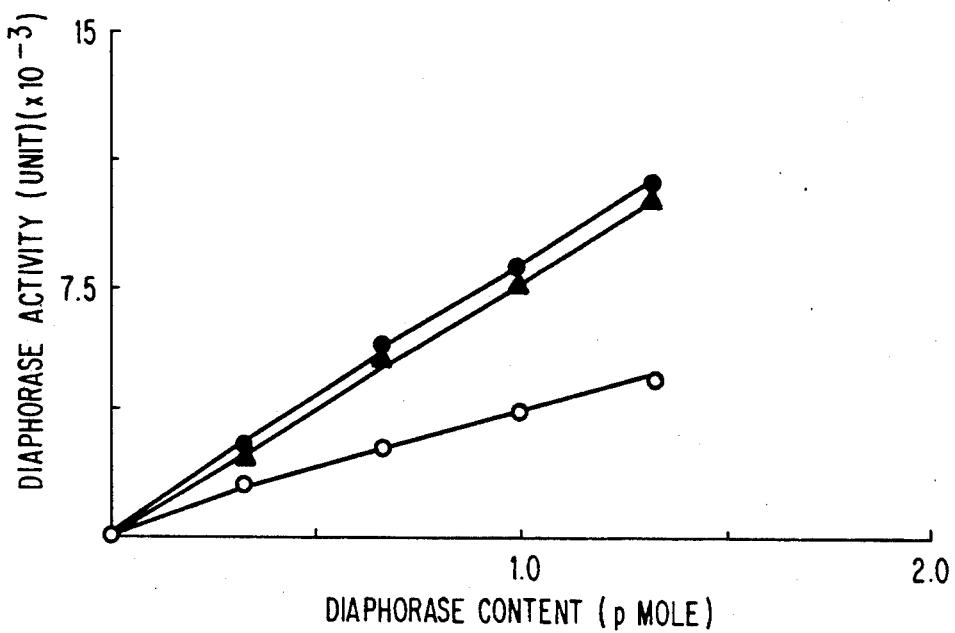
FIG. 3 is a graph showing the relationship between diaphorase amounts and diaphorase activities calculated from absorbancies.

After each solution was incubated at 30° C. for 3 minutes, 60 μl of 5 mM NBT was added thereto, followed by allowing the solution to react at 30° C. for 10 minutes. To the reaction system was added 150 μl of 1N HCl to stop the reaction, and an absorbance at 550 nm was measured. Diaphorase activities (unit) obtained from formula (1) are shown in Table 3 below and FIG. 3. In FIG. 3, the diaphorase content was plotted as the abscissa, and the diaphorase activity determined from the absorbance at 550 nm as the ordinate. Black not marks and black triangle marks indicate diaphorase activities which were obtained by using the solutions of the present invention containing CTAB as a surface active agent and EDTA and the solution containing STAC as a surface active agent and EDTA, respectively. White dot marks indicate diaphorase activities which were obtained by using the solution containing Triton-100 as a surface active agent.

TABLE 3

| Example No. | EDTA | Surface Active Agent | Diaphorase Content (P mole) | | | |
|---|---|---|---|---|---|---|
| | | | 0.33 | 0.67 | 1.00 | 1.33 |
| Example 2 | added | CTAB | 2.62 | 5.67 | 8.09 | 10.61 |
| Example 3 | added | STAC | 2.42 | 5.62 | 7.42 | 9.76 |
| Comparative Example 2 | not added | Triton X-100 | 1.51 | 2.67 | 3.72 | 4.74 |

P: pico

As is apparent from Table 3 and FIG. 3, where a reagent of the present invention containing CTAB (Example 2) or STAC (Example 3) and EDTA was used, the enzyme activity measured by a method of the present invention (i.e., as shown by absorbance values obtained by subtracting the respective blank from the respective measured value) increased to 1.7 times that of the Comparative Example at a diaphorase content of 10 ng and 2.2 times that of the Comparative Example at a diaphorase content of 40 ng, wherein the Comparative Example 2 reagent contained Triton X-100, indicating an increase in sensitivity of diaphorase activity measurement.

REFERENCE EXAMPLE 2

Polystyrene beads (available from Ichiko K.K.; diameter: 6.5 mm) were immersed in a 0.1 mg/ml solution of an anti-cancer embryonal antigen antibody (hereinafter abbreviated as anti-CEA antibody; available from Medics Co.) overnight and blocked by 1% bovine serum albumin to prepare anti-CEA antibody-fixed polystyrene beads.

One milligram of diaphorase (originated in Bacillus stearothermophilus; available from Unitika Ltd.) was reacted with 30 μg of succinimidyl 4-(N-maleimidomethyl)cyclohexan-1-carboxylate (available from ZIEBEN Chemical Co.) at pH 7 to introduce a maleimide group into diaphorase. The resulting modified diaphorase was mixed with 1.5 mg of anti-CEA antibody Fab' (prepared by digesting the antibody with pepsin followed by reducing) at pH 6 to crosslink the maleimide group and the —SH group to prepare a diaphorase-labeled anti-CEA antibody.

EXAMPLE 4 AND COMPARATIVE EXAMPLE 3

To the anti-CEA antibody-fixed polystyrene beads prepared in Reference Example 2 were added 50 μl of CEA having a concentration of 0, 5, 10 or 20 ng/ml and 200 μl of the diaphorase-labeled anti-CEA antibody having a concentration of 100 ng/ml, as prepared in Reference Example 2, followed by incubation at 37° C. for 18 hours for the antigen-antibody reaction. The liquid phase was removed, and the beads were thoroughly washed with a 20 mM sodium phosphate buffering solution (pH=7.2) containing 0.2% Tween 20, 0.2% bovine serum albumin, and 0.15M sodium chloride.

The following reagents were prepared.

Reagent of the Invention

| |
|---|
| Reagent A: 50 mM Triethanolamine-HCl (pH = 7.0) |
| 4 mM NADH |
| 10 mM EDTA |
| Reagent B: 50 mM Triethanolamine-HCl (pH = 7.0) |
| 10 mM NBT |
| 2% CTAB |

Comparative Reagent

| |
|---|
| Reagent A': 50 mM Triethanolamine-HCl (pH = 7.0) |
| 4 mM NADH |
| Reagent B': 50 mM Triethanolamine-HCl (pH = 7.0) |
| 10 mM NBT |
| 2% Triton X-100 |

To the beads was added 300 μl of Reagent A or A', followed by incubating at 30° C. for 3 minutes. Then, 300 μl of Reagent B or B' was added thereto, followed by incubation at 30° C. Ten minutes later, the reaction was stopped by addition of 150 μl of 1N HCl, and an absorbance of the assay solution at 550 nm was measured.

Figure 4:
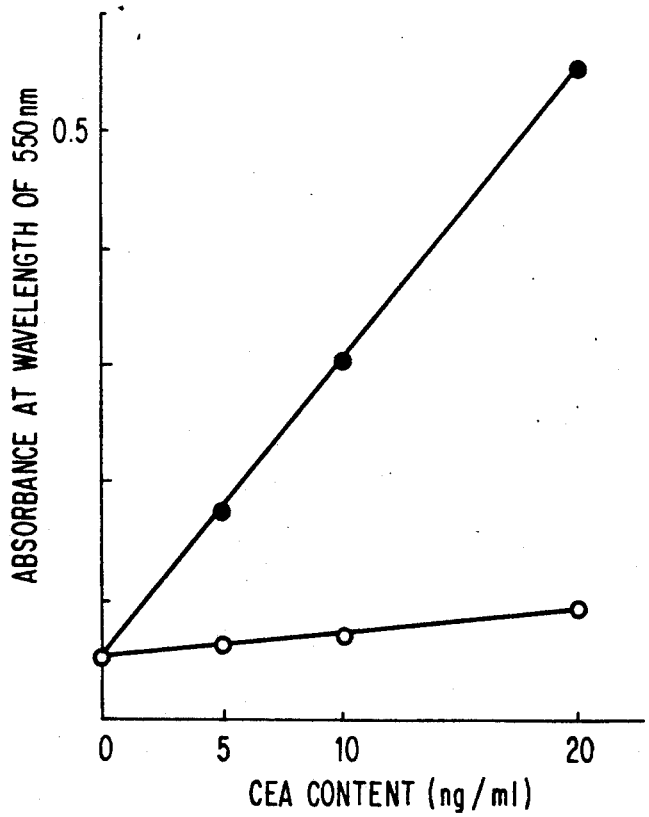
FIG. 4 is a graph showing the relationship between amounts of carcinoembryomic antigen (hereinafter abbreviated as CEA) and absorbencies.

The results obtained are shown in Table 4 below and FIG. 4. In FIG. 4, the CEA amount was plotted as the abscissa, and the absorbance at 550 nm as the ordinate. Black dot marks indicate diaphorase activities inclusive of blank values which were obtained by using the reagent containing CTAB and EDTA, and white dot marks indicate those obtained by using the comparative reagent containing Triton X-100.

TABLE 4

| Example No. | EDTA | Surface Active Agent | CEA Concentration (ng/ml) | | | |
|---|---|---|---|---|---|---|
| | | | 0 | 5 | 10 | 20 |
| Example 4 | added | CTAB | 0.050 | 0.175 | 0.303 | 0.554 |
| Comparative Example 3 | not added | Triton X-100 | 0.050 | 0.061 | 0.070 | 0.092 |

Further, coloring of the polystyrene beads due to adsorption of diformazan was not substantially observed in Example 4 wherein CTAB containing EDTA was used. In contrast, in Comparative Example 3 wherein Triton X-100 was used, the degree of coloring of the beads increased as the CEA concentration was increased.

Thus it is shown from Table 4 and FIG. 4 that diaphorase activity can be accurately measured even in the case where polystyrene beads are used as a solid phase in the diaphorase measurement system.

While the invention has been described in detail and with reference to specific examples thereof, it will be apparent to one skilled in the art that various changes and modifications can be made therein without departing from the spirit and scope thereof.

We claim:

1. A method for measuring diaphorase activity comprising
   (A) mixing a sample comprising diaphorase with nitroblue tetrazolium, a compound selected from the group consisting of EDTA and a salt thereof, at least one of nicotinamide adenine dinucleotide and nicotinamide adenine dinucleotide phosphate, and a surface active agent, to form an assay solution; and
   (B) measuring an increase relative to a blank standard in absorbance, due to the formation of diformazan, in said assay solution.

2. A method as claimed in claim 1, wherein said assay solution comprises about 1.0–50 mM of a compound selected from the group consisting of EDTA and a salt thereof.

3. A method as claimed in claim 1, wherein said assay solution comprises about 3–10 mM of a compound selected from the group consisting of EDTA and a salt thereof.

4. A method as claimed in claim 1, wherein said surface active agent is present in a concentration of about 0.05–5.0% by weight per volume.

5. A method as claimed in claim 4, wherein said surface active agent is present in a concentration of about 0.1–1.0% by weight per volume.

6. A method as claimed in claim 1, wherein said diaphorase is present in a concentration in said assay solution of about 0.002–0.2 U/ml.

7. A method as claimed in claim 1, wherein said surface active agent is a cationic surface active agent comprising a straight chain aliphatic saturated hydrocarbon, wherein said hydrocarbon
   (a) comprises from 14 to 28 carbon atoms; and
   (b) has a terminal trimethylammonium group.

8. A method as claimed in claim 7, wherein said cationic surface active agent is selected from the group consisting of cetyltrimethylammonium chloride, cetyltrimethylammonium bromide, stearyltrimethylammonium chloride and stearyltrimethylammonium bromide.

9. A method as claimed in claim 7, wherein said compound selected from the group consisting of EDTA and a salt thereof is present in a concentration of about 1–50 mM and said cationic surface active agent is present in a concentration of about 0.05–5.0% weight per volume.

10. A method as claimed in claim 9, wherein said compound selected from the group consisting of EDTA and a salt thereof is present in a concentration of about 3–10 mM and said cationic surface active agent is present in a concentration of about 0.1–1.0% weight per volume.

11. A reagent for measuring diaphorase activity comprising a first solution, a second solution, EDTA, and a surface active agent, wherein
   (A) said first solution comprises at least one of nicotinamide adenine dinucleotide or nicotinamide adenine dinucleotide phosphate; and
   (B) said second solution comprises nitroblue tetrazolium.

12. A reagent as claimed in claim 11, wherein said reagent has a final concentration of nicotinamide adenine dinucleotide or nicotinamide adenine dinucleotide phosphate of about 0.1–5.0 mM.

13. A reagent as claimed in claim 12, wherein said reagent has a final concentration of nicotinamide adenine dinucleotide or nicotinamide adenine dinucleotide phosphate of about 0.5–2.0 mM.

14. A reagent as claimed in claim 11, wherein said reagent has a final concentration of a compound selected from the group consisting of EDTA and a salt thereof of about 1.0–50 mM.

15. A reagent as claimed in claim 14, wherein said reagent has a final concentration of a compound selected from the group consisting of EDTA and a salt thereof of about 3.0–10 mM.

16. A reagent as claimed in claim 11, wherein said reagent has a final concentration of said surface active agent of about 0.05–5.0% by weight per volume, and a final concentration of nitroblue tetrazolium of about 0.1–10 mM.

17. A reagent as claimed in claim 11, wherein said reagent has a final concentration of said surface active agent of about 0.1–1.0% by weight per volume, and a final concentration of nitroblue tetrazolium of about 0.1–10 mM.

18. A reagent as claimed in claim 11, wherein said surface active agent is a cationic surface active agent comprising a straight chain aliphatic saturated hydrocarbon comprising from 14 to 28 carbon atoms, wherein said hydrocarbon has a terminal trimethylammonium group.

19. A reagent as claimed in claim 18, wherein said cationic surface active agent is selected from the group consisting of cetyltrimethylammonium chloride, cetyltrimethylammonium bromide, stearyltrimethylammonium chloride and stearyltrimethylammonium bromide.

20. A method as claimed in claim 1, wherein said diaphorase is present in a concentration of no more than 2.0 U/ml in said sample.

* * * * *